United States Patent [19]

van Andel

[11] Patent Number: Plant 6,786

[45] Date of Patent: May 9, 1989

[54] CARNATION NAMED STATORNA

[75] Inventor: Jacob van Andel, Aalsmeer, Netherlands

[73] Assignee: Van Staaveren B.V., Aalsmeer, Netherlands

[21] Appl. No.: 101,854

[22] Filed: Sep. 28, 1987

[51] Int. Cl.[4] ..... A01H 5/00

[52] U.S. Cl. ..... Plt./73

[58] Field of Search ..... Plt./70, 72–73

*Primary Examiner*—Robert E. Bagwill

*Attorney, Agent, or Firm*—Charles W. Rummler

[57] ABSTRACT

A new carnation variety particularly distinguished by the solid dark red coloration of its very large semi-spherical blooms which are borne on long, strong, upright stems on a plant which blooms continuously with a strong, upright growth habit with abundant foliage, an average height of about 150 cm., and strong resistance to diseases.

1 Drawing Sheet

BACKGROUND OF THE NEW PLANT

This new carnation cultivar originated as a sport of the unpatented variety 'Stanti' at Aalsmeer, Holland, and was selected by me for propagation and test because of the very large size and bright red coloration of its blooms. This plant was propagated by me and under my direction at Aalsmeer, by means of cuttings through several successive generations, which demonstrated that the novel and distinctive characteristics of this plant would hold true from generation to generation and appeared to be firmly fixed.

DESCRIPTION OF THE DRAWING

This new carnation plant is illustrated by the accompanying photographic drawing which shows, in full color, a three-quarter face view of a typical flower illustrating the dense character of its mass of petals and its solid overall coloration, the colors shown being as nearly true to those specified herein as is reasonably possible to obtain by conventional photographic procedures.

DESCRIPTION OF THE NEW PLANT

The following is a detailed description of my new carnation variety based upon observation of greenhouse grown plants made at Aalsmeer, Holland, the color designations being specified herein according to the R.H.S. Colour Chart published by The Royal Horticultural Society of London, England.

THE PLANT

Origin: Sport.
Parentage: The unpatented variety 'Stanti'.
Classification: *Dianthus caryophyllus.*
Form: Tall, upright bush.
Height: Depends upon season, averaging about 150 cm.
Main stem length: About 80 to 120 cm., depending upon season.
Growth habit: Upright with good strength and normal branching character.
Foliage:
- *Quantity.*—Abundant, the number of leaves depending upon season.
- *Leaf size.*—Varies; about 18 cm. long and about 0.8 cm wide.

- *Shape.*—Linear with acuminate tip and entire margins, the leaves being weakly curled.
- *Texture.*—Smooth.
- *Color.*—Upper side and under side — Blue-Green with a waxy layer.

THE BUD

Form: Cylindrical and pointed.
Size: Medium.
- *Diameter.*—About 1.5 cm.
- *Length.*—About 3 to 3.5 cm.

Sepals:
- *Number.*—Normal for carnations.
- *Character.*—The sepals curl back when the flowers open.
- *Color.*—Inside and outside — Grey/Green.

Calyx:
- *Shape.*—Long pointed.
- *Size.*—Large.
- *Splitting.*—Rarely.
- *Aspect.*—Smooth.

THE FLOWER

Blooming habit: Continuous from Spring through Fall.
Size of flower: Very large.
- *Diameter.*—About 9 cm.
- *Depth.*—About 4 to 4.5 cm.

Borne: Singly.
Shape: When bloom first opens, high centered. When bloom matures, high centered.
Petalage:
- *Number of petals.*—About 50 to 70.
- *Arrangement.*—Ruffled and imbricated.
- *Form.*—Obovate with lightly ruffled margins.
- *Texture.*—Soft.
- *Appearance.*—Satiny.
- *Color.*—45 D throughout all petals.

Peduncle or flower stem:
- *Length.*—Depends on season.
- *Character.*—Strong and upright.
- *Color.*—Dark Grey/Green.

Persistence: The flowers hang on and dry.
Fragrance: Weak.
Lasting quality: About three weeks on the plant and about ten to fifteen days as a cut flower.

THE REPRODUCTIVE ORGANS

Stamens:

*Number.*—About average for carnations.
*Arrangement.*—Around the ovary.
*Anthers.*—Size: Average. Color: Cream.
*Filaments.*—Various lengths.
*Pollen.*—There is no pollen.

Pistils:

*Number.*—One.
*Styles.*—Of average length. Color: White with red.

*Stigmas.*—Color: White.
Character of ovary: Normal.

I claim:

1. The new and distinct carnation cultivar and the parts thereof, substantially as herein shown and described, characterized by the uniform overall bright red coloration of its very large flowers, which are carried on long, straight, stiff stems; and by its tall, upright growth habit with good strength and abundant foliage.

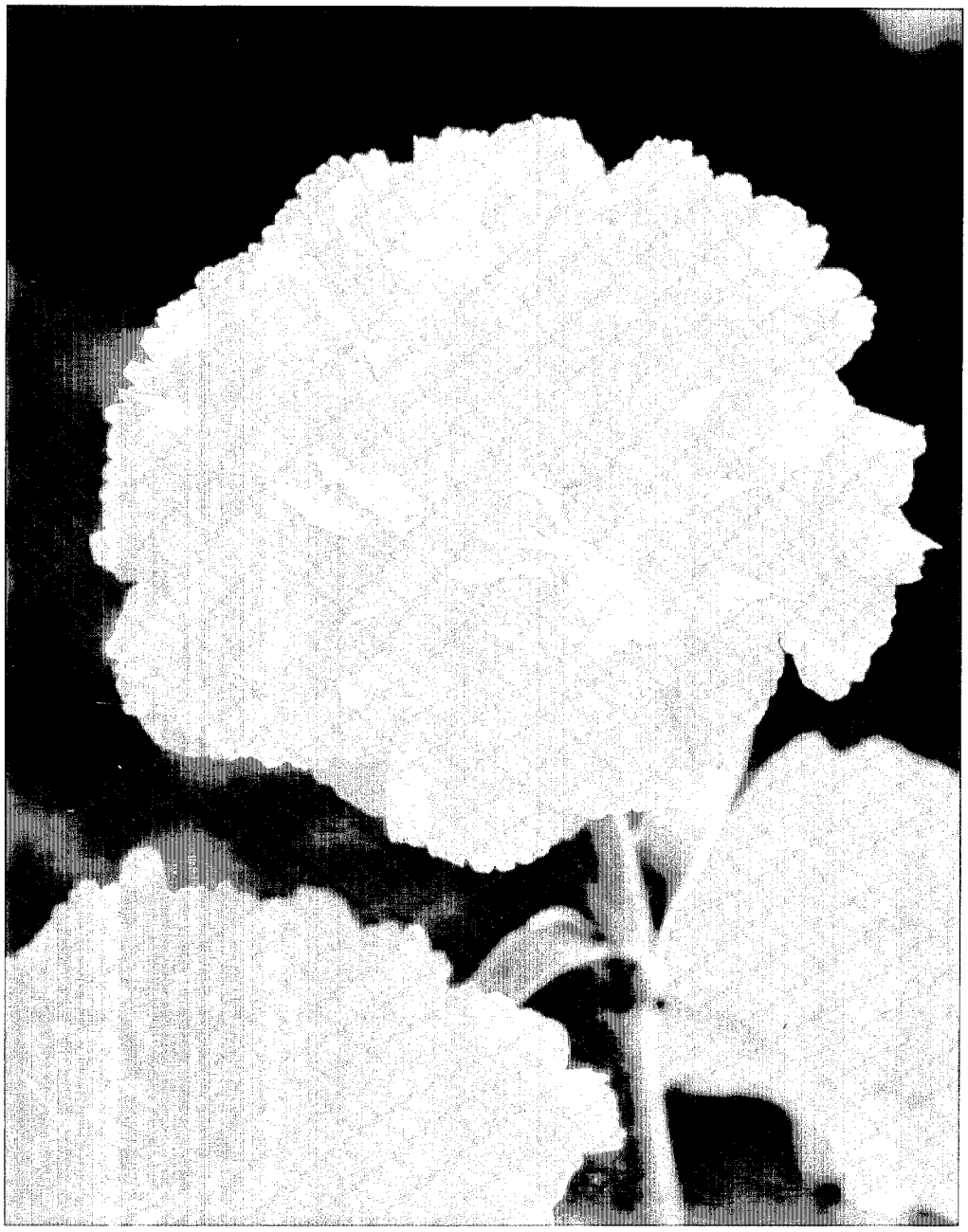

* * * * *